United States Patent
Davidson et al.

(10) Patent No.: US 6,689,156 B1
(45) Date of Patent: Feb. 10, 2004

(54) STENT RANGE TRANSDUCERS AND METHODS OF USE

(75) Inventors: Charles J. Davidson, Winnetka, IL (US); Gil M. Vardi, Chesterfield, MO (US); Eric Williams, Evanston, IL (US); Stephen Kao, Mountain View, CA (US); Niyazi U. Behyan, Santa Clara, CA (US)

(73) Assignee: Advanced Stent Technologies, Inc., Pleasanton, CA (US)

( * ) Notice: Subject to any disclaimer, the term of this patent is extended or adjusted under 35 U.S.C. 154(b) by 0 days.

(21) Appl. No.: 09/669,060

(22) Filed: Sep. 22, 2000

Related U.S. Application Data
(60) Provisional application No. 60/155,611, filed on Sep. 23, 1999.

(51) Int. Cl.$^7$ .................................................. A61F 2/06
(52) U.S. Cl. ...................... 623/1.11; 606/108; 606/194
(58) Field of Search ............................... 623/1.11, 1.35, 623/1.23; 606/108, 191–192, 194–195, 198; 600/433–435, 437, 442–443, 449, 459, 462–463, 466–468, 470, 585–587; 604/96.01, 164.13

(56) References Cited

U.S. PATENT DOCUMENTS

| | | | |
|---|---|---|---|
| 1,596,754 A | 8/1926 | Mochelle | |
| 3,872,893 A | 3/1975 | Roberts | |

(List continued on next page.)

FOREIGN PATENT DOCUMENTS

| | | | | |
|---|---|---|---|---|
| DE | 29701758 U1 | * | 3/1997 | ............. A61F/2/06 |
| EP | 804907 | | 5/1997 | |
| EP | 876805 | | 11/1998 | |
| EP | 1031328 A1 | | 8/2000 | |
| EP | 1031330 A2 | | 8/2000 | |
| FR | 2678508 A1 | * | 1/1993 | ............. A61F/2/06 |
| WO | WO 88/06026 | | 2/1988 | |
| WO | WO 92/19308 | | 11/1992 | |
| WO | WO 96/41592 | | 6/1996 | |
| WO | WO 97/33532 | | 3/1997 | |
| WO | WO 97/45073 | | 5/1997 | |
| WO | WO 98/17204 | | 4/1998 | |
| WO | WO 98/19628 | | 5/1998 | |
| WO | WO 98/35634 | | 8/1998 | |
| WO | WO 98/36709 | | 8/1998 | |
| WO | WO 98/44871 | | 10/1998 | |
| WO | WO 98/48733 | | 11/1998 | |
| WO | WO 98/52497 | | 11/1998 | |
| WO | WO 99/17680 | | 4/1999 | |
| WO | WO 99/34749 | | 7/1999 | ............. A61F/2/06 |
| WO | WO 99/39661 | | 8/1999 | |
| WO | WO 99/65419 | | 12/1999 | |
| WO | WO 00/00104 | | 1/2000 | |
| WO | WO 00/12166 | | 3/2000 | |
| WO | WO 00/13613 | | 3/2000 | |
| WO | WO 00/53122 | | 9/2000 | |

OTHER PUBLICATIONS

Supplementary European Search report for Application No. EP 00 96 6881, Apr. 29, 2003.

(List continued on next page.)

*Primary Examiner*—David J. Isabella
*Assistant Examiner*—Urmi Chattopadhyay
(74) *Attorney, Agent, or Firm*—Patton Boggs L.L.P.

(57) ABSTRACT

A system and method for delivering and positioning a stent within a bifurcated body lumen includes a stent delivery system including a catheter, expansion device, a stent with a side hole disposed on the expansion device, and an ultrasound transducer disposed between the expansion device and the stent. The ultrasound transducer is configured for transmitting and receiving signals and for imaging of a body lumen so as to locate an ostium of a branch vessel and facilitate alignment of the stent side hole with the ostium.

17 Claims, 9 Drawing Sheets

U.S. PATENT DOCUMENTS

| | | |
|---|---|---|
| 4,140,126 A | 2/1979 | Choudhury |
| 4,410,476 A | 10/1983 | Redding et al. |
| 4,413,989 A | 11/1983 | Schjeldahl |
| 4,421,810 A | 12/1983 | Rasmussen |
| 4,503,569 A | 3/1985 | Dotter |
| 4,681,570 A | 7/1987 | Dalton |
| 4,689,174 A | 8/1987 | Lupke |
| 4,733,665 A | 3/1988 | Palmaz |
| 4,739,762 A | 4/1988 | Palmaz |
| 4,759,748 A | 7/1988 | Reed .......................... 604/95 |
| 4,769,029 A | 9/1988 | Patel |
| 4,872,874 A | 10/1989 | Taheri |
| 4,900,314 A | 2/1990 | Quackenbush |
| 4,957,501 A | 9/1990 | Lahille et al. |
| 4,957,508 A | 9/1990 | Kaneko et al. |
| 4,994,071 A | 2/1991 | MacGregor |
| 5,042,976 A | 8/1991 | Ishitsu et al. |
| 5,054,501 A | 10/1991 | Chuttani et al. |
| 5,061,240 A | 10/1991 | Cherian |
| 5,064,435 A | 11/1991 | Porter |
| 5,102,403 A | 4/1992 | Alt |
| 5,104,404 A | 4/1992 | Wolff |
| 5,117,831 A | 6/1992 | Jang |
| 5,122,125 A | 6/1992 | Deuss |
| 5,147,317 A | 9/1992 | Shank et al. |
| 5,159,920 A | 11/1992 | Condon et al. |
| 5,217,440 A | 6/1993 | Frassica |
| 5,244,619 A | 9/1993 | Burnham |
| 5,263,932 A | 11/1993 | Jang |
| 5,282,472 A | 2/1994 | Companion et al. |
| 5,304,220 A | 4/1994 | Maginot |
| 5,337,733 A | 8/1994 | Bauerfeind et al. |
| 5,342,297 A | 8/1994 | Jang |
| 5,387,235 A | 2/1995 | Chutner |
| 5,404,887 A | 4/1995 | Prather |
| 5,409,458 A | 4/1995 | Khairkhahan et al. |
| 5,413,586 A | 5/1995 | Dibie et al. |
| 5,417,208 A | 5/1995 | Winkler |
| 5,443,497 A | 8/1995 | Venbrux |
| 5,445,624 A | 8/1995 | Jiminez |
| 5,449,373 A | 9/1995 | Pinchasik et al. |
| 5,449,382 A | 9/1995 | Dayton |
| 5,456,712 A | 10/1995 | Maginot |
| 5,462,530 A | 10/1995 | Jang |
| 5,489,295 A | 2/1996 | Piplani et al. |
| 5,496,292 A | 3/1996 | Burnham |
| 5,507,769 A | 4/1996 | Marin et al. |
| 5,522,801 A | 6/1996 | Wang |
| 5,531,788 A | 7/1996 | Dibie et al. |
| 5,545,132 A | 8/1996 | Fagan et al. |
| 5,562,724 A | 10/1996 | Vorwerk et al. |
| 5,562,725 A | 10/1996 | Schmitt et al. |
| 5,575,818 A | 11/1996 | Pinchuk |
| 5,593,442 A | 1/1997 | Klein |
| 5,607,444 A | 3/1997 | Lam |
| 5,609,627 A | 3/1997 | Goicoechea |
| 5,613,980 A | 3/1997 | Chauhan .................... 606/194 |
| 5,613,981 A | 3/1997 | Boyle et al. |
| 5,617,878 A | 4/1997 | Taheri |
| 5,628,788 A | 5/1997 | Pinchuk |
| 5,632,763 A | 5/1997 | Glastra |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,693,084 A | 12/1997 | Chutter |
| 5,693,086 A | 12/1997 | Goicoechea et al. |
| 5,707,354 A | 1/1998 | Salmon |
| 5,709,713 A | 1/1998 | Evan et al. |
| 5,716,365 A | 2/1998 | Goicoechea et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A * | 3/1998 | Yock et al. .................. 600/437 |
| 5,733,303 A | 3/1998 | Israel et al. |
| 5,749,825 A | 5/1998 | Fischell et al. |
| 5,749,848 A * | 5/1998 | Jang et al. ............... 604/103.1 |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,800,508 A | 9/1998 | Goicoechea et al. |
| 5,824,036 A | 10/1998 | Lauterjung |
| 5,824,040 A | 10/1998 | Cox et al. |
| 5,824,044 A | 10/1998 | Quiachon et al. |
| 5,827,320 A | 10/1998 | Richter et al. |
| 5,836,966 A | 11/1998 | St. Germain |
| 5,843,031 A | 12/1998 | Hermann et al. ............. 604/95 |
| 5,846,204 A * | 12/1998 | Solomon .................... 600/463 |
| 5,851,210 A | 12/1998 | Torossian |
| 5,865,178 A | 2/1999 | Yock |
| 5,868,777 A | 2/1999 | Lam |
| 5,891,133 A * | 4/1999 | Murphy-Chutorian ......... 606/7 |
| 5,897,588 A | 4/1999 | Hull et al. |
| 5,906,640 A | 5/1999 | Penn et al. |
| 5,913,895 A | 6/1999 | Burpee et al. |
| 5,913,897 A | 6/1999 | Corso, Jr. et al. |
| 5,922,020 A | 7/1999 | Klein et al. |
| 5,928,248 A | 7/1999 | Acker ........................ 606/108 |
| 5,938,682 A | 8/1999 | Hojeibane |
| 5,961,548 A | 10/1999 | Shmulewitz |
| 5,967,986 A * | 10/1999 | Cimochowski et al. ..... 600/454 |
| 5,972,018 A | 10/1999 | Israel et al. |
| 6,013,091 A | 1/2000 | Ley et al. |
| 6,017,363 A | 1/2000 | Hojeibane |
| 6,030,414 A | 2/2000 | Taheri |
| 6,033,434 A | 3/2000 | Borghi |
| 6,036,682 A | 3/2000 | Lange et al. |
| 6,039,749 A | 3/2000 | Marin et al. |
| 6,048,361 A | 4/2000 | VanOepen |
| 6,096,073 A | 8/2000 | Webster et al. |
| 6,099,497 A | 8/2000 | Adams |
| 6,129,738 A | 10/2000 | Lashinski et al. |
| 6,165,195 A | 12/2000 | Wilson et al. |
| 6,210,429 B1 * | 4/2001 | Vardi et al. ................. 623/1.11 |
| 6,398,792 B1 * | 6/2002 | O'Connor ................... 600/470 |

OTHER PUBLICATIONS

SCIMED Life Systems, Inc.—TRIO™ 14 PTCA Catheter, Re–engineering Over–the–Wire Balloon Technology, Company Brochure, 1994.

Caputo et al., "Stent Jail: A Minimum–Security Prison" The American Journal of Cardiology, (1996) 7:1226–1230.

Fischman et al., "A Randomized Comparison of Coronary–Stent Placement and Balloon Angioplasty in the Treatment of Coronary Artery Disease" The New England Journal of Medicine, (1994) 331(8): 496–501.

Nakamura et al., "Techniques for Palmaz–Schatz Stent Deployment in Lesions with a Large Side Branch" Catheterization & Cardiovascular Diagnosis, (1995) 34:353–361.

Serruys et al., "A Comparison of Balloon–Expandable–Stent Implantation with Balloon Angioplasty in Patients with Coronary Artery Disease" The New England Journal of Medicine, (1994) 331(8): 489–495.

Colombo et al., "Kissing' Stents for Bifurcational Coronary Lesion" Catheterization and Cardiovascular Diagnosis, (1993) 30:327–330.

Carrie et al., "T'–Shaped Stent Placement": A Technique for the Treatment of Dissected Bifurcation Lesions Catheterization and Cardiovascular Diagnosis, (1996) 37:311–313.

Katoh et al., "New Double Wire Technique to Stent Ostial Lesions" Catheterization and Cardiovascular Diagnosis, (1997) 40:400–402.

Lewis et al., "Acute Procedural Results in the Treatment of 30 Coronary Artery Bifurcation Lesions with a Double–Wire Atherectomy Technique for Side Branch Protection", *American Heart Journal* (1994) 127:1600–1607.

* cited by examiner

STENT RANGE TRANSDUCERS AND METHODS OF USE

This application claims the benefit of U.S. Provisional Application No. 60/155,611 filed on Sep. 23, 1999, the complete disclosure of which is incorporated herein by reference.

CROSS-REFERENCES TO RELATED APPLICATIONS

This application is being filed concurrently with related U.S. patent application Ser. No. 09/668,687, entitled "Differentially Expanding Stent and Methods of Use"; and U.S. patent application Ser. No. 09/668,832, entitled, "Bifurcation Stent Systems and Methods," the complete disclosures of which are incorporated herein by reference and filed at a date even herewith.

BACKGROUND OF THE INVENTION

A type of endoprosthesis device, commonly referred to as a stent, may be placed or implanted within a vein, artery or other hollow body organ or lumen for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al., *New England Journal of Medicine* 331: 489–495 (1994) and Fischman, D L et al. *New England Journal of Medicine* 331:496–501 (1994)). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device which is intraluminally implanted within bodily vessels to reinforce collapsing, dissected, partially occluded, weakened, diseased or abnormally dilated or small segments of a vessel wall.

One of the drawbacks of conventional stents is that they are difficult to position. In general, positioning a stent involves moving the stent to the desired position and then maintaining the position while the stent is deployed. Accurate positioning is critical to proper operation of the stent. For example, the use of such stents to treat diseased vessels at or near a bifurcation (branch point) of a vessel requires very accurate positioning otherwise, there is a potential for compromising the degree of patency of the main vessel and/or its branches, or the bifurcation point. Compromising the bifurcation point limits the ability to insert a branch stent into the side branch if the result of treatment of the main vessel is suboptimal. Suboptimal results may occur as a result of several mechanisms, such as displacing diseased tissue, plaque shifting, vessel spasm, dissection with or without intimal flaps, thrombosis, and embolism.

In light of the foregoing, it would be desirable to provide methods, apparatus and/or systems to increase stent positioning accuracy, particularly when used with bifurcated body lumens.

SUMMARY OF THE INVENTION

The present invention provides exemplary apparatus, systems and methods for accurately delivering and positioning a stent within a body lumen, particularly within a bifurcated body lumen. In one embodiment, a stent delivery system according to the present invention includes a catheter comprising a catheter body having a distal end, a proximal end, a longitudinal axis and a lumen. An expansion device, which in one embodiment is a balloon, is disposed near the catheter body distal end, and a stent having a side hole is disposed over the expansion device. An ultrasound transducer is disposed near the catheter body distal end and positioned for transmitting and receiving ultrasound signals through the side hole. In this manner, an intravascular ultrasound catheter and system is used to help properly position the stent, and properly align the stent side hole with a branch vessel.

The ultrasound transducer is disposed inside the expansion device, or between the expansion device and stent in alternative embodiments. Preferably, the ultrasound transducer is adapted to be axially translated along the longitudinal axis and/or rotated relative to the longitudinal axis. In this manner, the ultrasound transducer may be used to image surrounding fluids and tissue to assure proper stent alignment.

In some embodiments, the stent delivery system further includes a transducer housing to which the transducer is coupled. The housing has distal and proximal ends, with a passageway passing therethrough. The passageway has a guidewire partially disposed therein in one embodiment. The housing proximal end is coupled to a drive cable, which in one embodiment is adapted to rotate the housing relative to the catheter distal end. A controller may be included, coupled to the transducer, to facilitate system operation.

The present invention further provides methods of positioning a stent having a side opening. In one embodiment, the method includes providing a stent delivery system ostensibly as described herein, positioning the stent delivery system in a body lumen, imaging the body lumen with the transducer to locate an ostium of a branch vessel, and aligning the stent side hole with the ostium. In this manner, the use of ultrasound imaging facilitates proper stent side hole alignment with the branch vessel.

In one embodiment, the ultrasound transducer is adapted to rotate relative to the longitudinal axis. The imaging further includes rotating the transducer to image a cross section of the body lumen. Similarly, in one embodiment, aligning the stent side hole includes axially translating the stent along the longitudinal axis and/or rotating the stent about the longitudinal axis. In some embodiments, a body lumen guidewire is introduced, and the catheter is advanced over the guidewire to be near the branch vessel.

In one embodiment, the stent delivery system is conveniently part of a kit, which includes instructions for use setting forth a method for positioning the stent in a bifurcated body lumen so that the side hole is substantially aligned with an ostium of a branch vessel.

Other objects, features and advantages of the present invention will become more fully apparent from the following detailed description, the appended claims and the accompanying drawings.

DESCRIPTION OF THE SPECIFIC EMBODIMENTS

Figure 1:
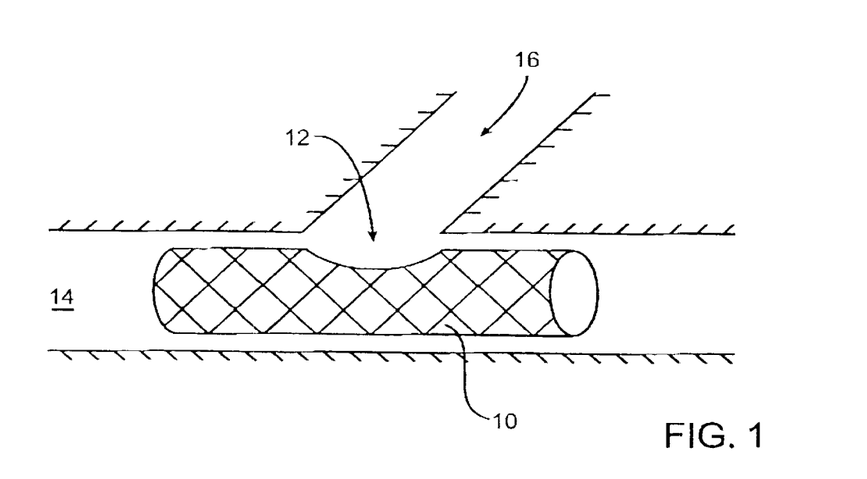
FIG. 1 depicts an overall view of a stent according to the present invention disposed in a body lumen.
Figure 2:
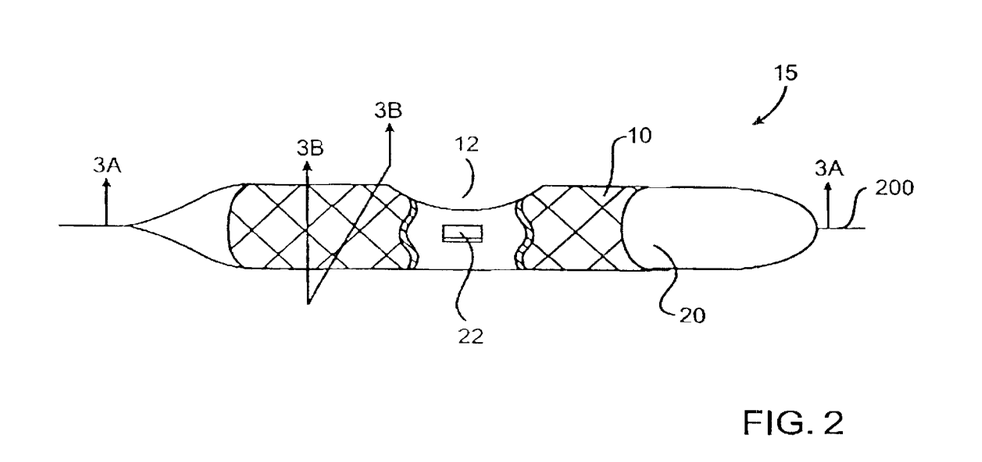
FIG. 2 depicts an overall view of a stent delivery apparatus according to the present invention.

FIG. 1 depicts a simplified view showing a stent 10 disposed within a main vessel 14. Main vessel 14 may comprise an artery, a vein or a wide range of body lumens into which it is desirable to dispose stent 10. Stent 10 includes a side hole 12, which is in registry with an ostium of a branch vessel 16. In many cases, it is desirable to have side hole 12 aligned with the ostium of branch vessel 16 to, for example, permit the introduction of a branch stent or second stent (not shown) into branch vessel 16. The alignment of side hole 12 with branch vessel 16 is often crucial to the proper use of stent 10, and prior art methods for alignment are replete with problems. Apparatus, systems and methods of the present invention are directed, in part, to properly aligning side hole 12 with branch vessel 16 by using an imaging transducer or catheter with stent 10.

Figure 3A:
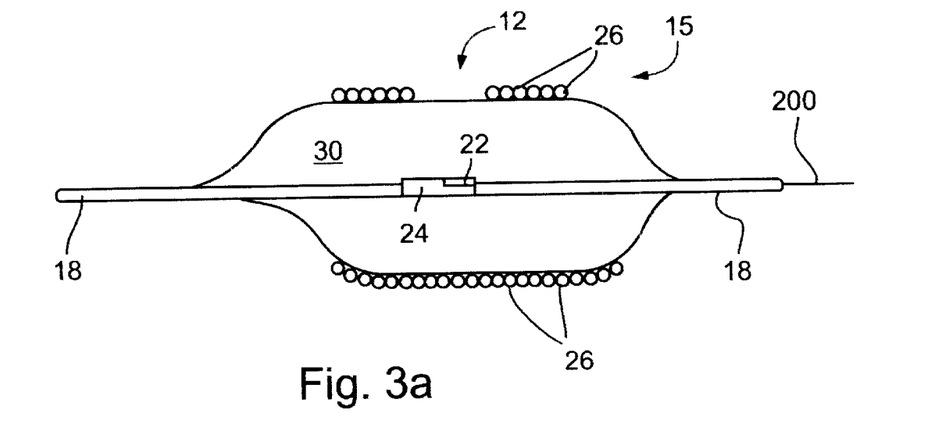
FIGS. 3A, 3B and 3C provide side and front cross-sectional views of embodiments of the apparatus shown in FIG. 2, FIGS. 4A and 4B depict an overall view and a side cross-sectional view, respectively, of an ultrasound imaging device according to the present invention.
Figure 3B:
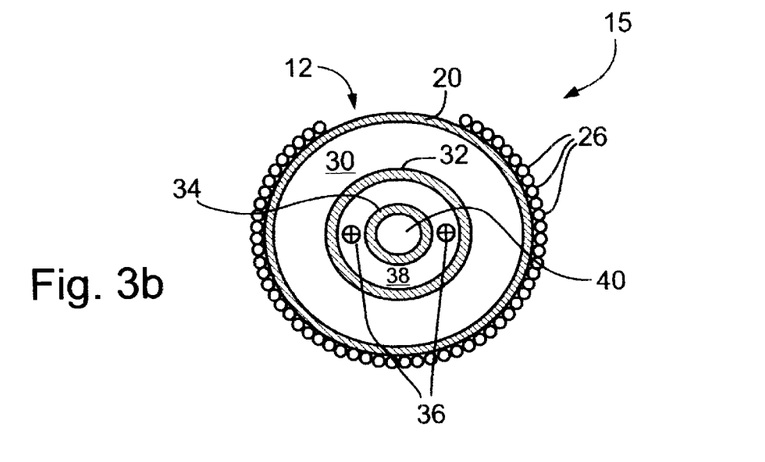
Figure 3C:
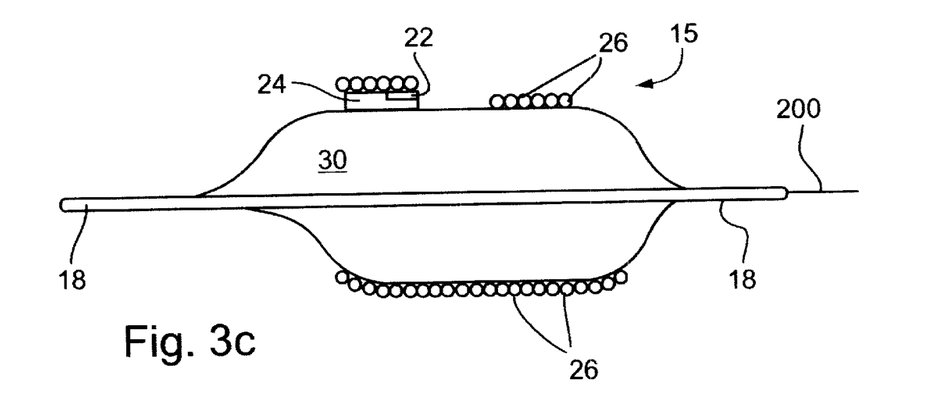

Turning now to FIGS. 2, 3A, 3B, 3C, 4A and 4B, an exemplary stent delivery system 15 according to the present invention will be described. Stent 10 is shown in a non-expanded state, crimped around a balloon 20. Balloon 20 provides a mechanism for expanding stent 10 when stent 10 is placed at a desired location within a body lumen. It will be appreciated by those skilled in the art that other methods of expanding stent 10 fall within the scope of the invention. System 15 further includes a transducer 22 to provide an imaging capability to help properly position side hole 12. Transducer 22 typically comprises piezoelectric materials for the conversion of electrical signals into mechanical energy, more specifically, sound energy. As best shown in FIG. 3A, transducer 22 is coupled to a housing 24. In one embodiment, housing 24 is disposed within balloon 20, as shown in FIG. 3A. Transducer housing 24 is positioned so that ultrasound signals transmitted from transducer 22 pass through side hole 12 into the surrounding fluid or tissue. In this manner, and as further described below, transducer 22 may be used to indicate when side hole 12 is properly aligned with a branch vessel 16 as opposed to facing a wall of main vessel 14. In an ii alternative embodiment, as shown in FIG. 3C, transducer 2 is mounted on an outer surface of balloon 25 or positioned between balloon 25 and stent 10. For example, transducer 22 may be mounted on balloon 25 within sidehole 12. In one embodiment, a guidewire 18 is disposed through balloon 20, and is used to help guide the stent delivery system to a desired region within a body lumen.

Turning now to FIG. 3B, a cross-sectional view taken along line 3B—3B is shown. Stent 10 comprises a plurality of struts 26 configured in a desired relationship. It will be appreciated by those skilled in the art that the precise configuration of stent struts 26 may vary widely within the scope of the present invention. Further, the present invention may use stent configurations disclosed in U.S. application Ser. No. 09/668,687, and U.S. patent application Ser. No. 09/668,832, the complete disclosures of which have been previously incorporated by reference. Stent 10, including struts 26, are crimped around balloon 20. The imaging catheter, which includes transducer 22, is disposed within a balloon lumen 30 inside balloon 25. The imaging apparatus has an outer member 32 and an inner member 34 defining a wire lumen 38 therebetween. A passageway 40 is formed within inner member 34. Wire lumen 38 is used to maintain transducer wires 36, which typically connect opposing faces of transducer 22 with a controller (not shown). Passageway 40, in one embodiment, defines a guidewire lumen 40 through which guidewire 18 extends. In this manner, guidewire 18 extends through housing 24 to facilitate proper alignment between transducer 22 and stent 10.

Transducer housing 24 is adapted to be translated axially along a longitudinal axis 200. In one embodiment, the axial translation of transducer housing 24 is made relative to stent 10. Alternatively, balloon 20 and transducer housing 24 are disposed such that they move in parallel, maintaining the proper configuration of transducer 22 with respect to side hole 12.

Figure 4A:
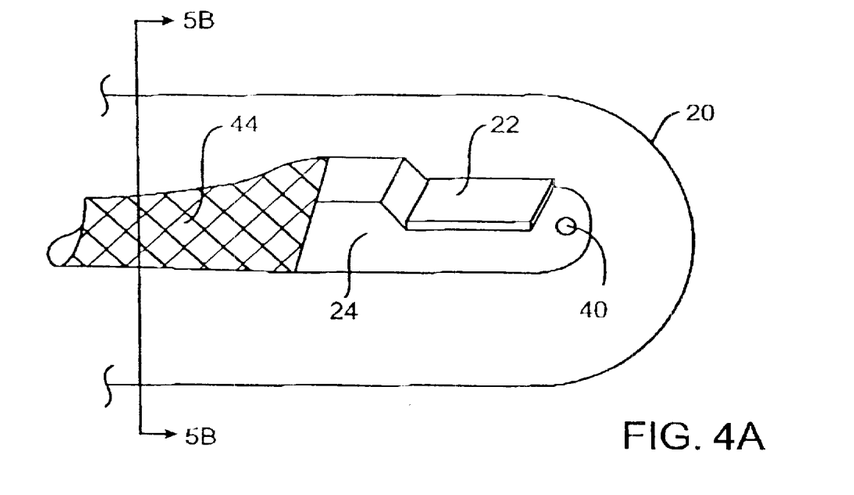
Figure 4B:
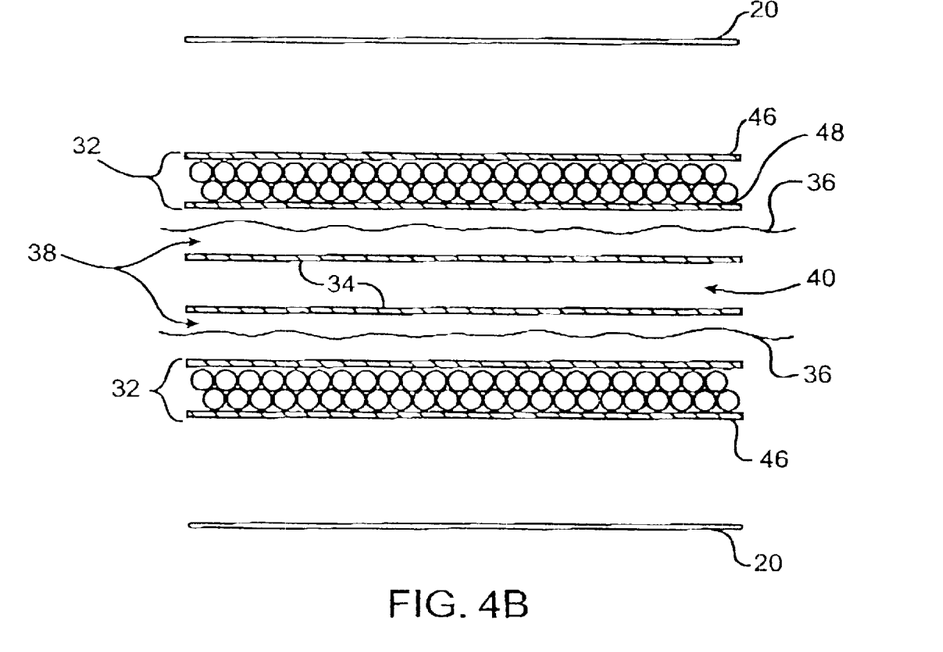

FIGS. 4A and 4B depict additional details of transducer 22 and housing 24. In one embodiment, a drive cable 44 is coupled to a proximal end of housing 24. FIG. 4A further depicts passageway 40 which extends through housing 24. In one embodiment, drive cable 44 comprises two counter-wound cables made of stainless steel, nitinol or the like. Such a drive cable facilitates its introduction into tortuous vasculatures. Drive cable 44 further permits rotation of housing 24, and hence the rotation of transducer 22. Preferably, such rotation is made relative to longitudinal axis 200

FIG. 4B is a side cross-sectional view of a portion of the imaging catheter. As shown, an optional sheath 46 may be used to enclose drive cable 44. Sheath 46 operates to protect balloon 20 during rotation of drive cable 44. Further, sheath 46 provides a substantially smooth outer surface for embodiments in which the imaging apparatus is translated axially relative to balloon 20 and/or stent 10. Sheath 46 may comprise polyethylene, as well as a wide range of other materials. In one embodiment, sheath 46, drive cable 44 and an inner sleeve 48 correspond to outer member 32 depicted in FIG. 3B.

Drive cable 44 defines wire lumen 38 into which transducer wires 36 are disposed. Inner member 34 maintains transducer wires 36 within wire lumen 38. Further, inner member 34 defines passageway 40 through which guidewire 18 may be disposed. In an alternative embodiment, guidewire 18 passes through balloon lumen 30, adjacent to drive cable 44 or sheath 46.

Figure 5A:
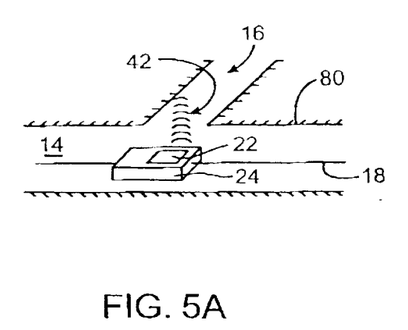
FIGS. 5A and 5B depict simplified views of a stent delivery system according to the present invention disposed in a body lumen.
Figure 5B:
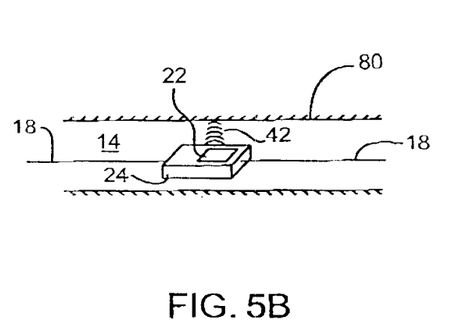
Figure 5C:
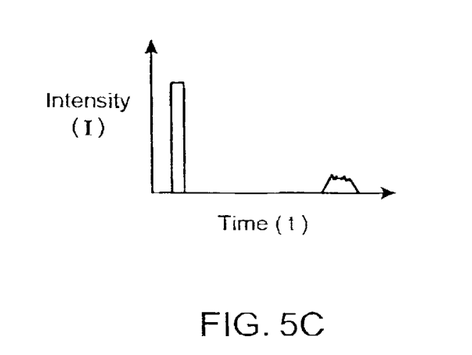
FIGS. 5C and 5D plot transmitted and received ultrasound energy signals as a function of time for stent delivery systems positioned according to FIGS. 5A and 5B, respectively.
Figure 5D:
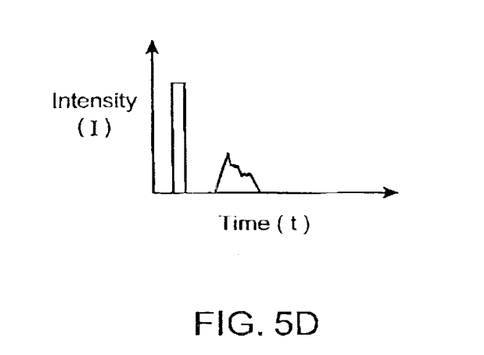

FIGS. 5A and 5B depict a simplified view of the imaging of a body lumen with transducer 22. Similarly, FIGS. 5C and 5D depict the intensity of transmitted and reflected signals when transducer 22 is activated at the positions shown in FIGS. 5A and 5B, respectively. For example, in FIG. 5A, a voltage is applied across transducer 22 to generate ultrasound signals 16 which are transmitted from transducer 22 to surrounding fluids and tissue. When signals 16 encounter a change in medium, and more specifically a change in the density of the material through which the signals are passing, at least a portion of signal 16 is reflected back toward transducer 22. Transducer 22 receives the reflected signal and transmits a corresponding voltage through wires 36 to a controller (not shown) for processing. When transducer 22 is positioned as shown in FIG. 5A, signals 16 travel down a portion of the branch vessels 16 before being reflected by a vessel wall, occlusion, or the like. Hence, as can be seen in FIG. 5C, the reflected signal is received after some time delay relative to the initial signal pulse. Additionally, the travel time for the reflected signal results in much of the sound energy being lost in blood or other fluid. Hence a comparatively weak signal is returned to transducer 22. Correspondingly, if transducer 22 is disposed adjacent a wall 80, such as shown in FIG. 5B, the reflected signal is received much sooner and occurs at a greater intensity than the alignment shown in FIG. 5A. The stronger echo or return signal is depicted in FIG. 5D. In this manner, ultrasound imaging, including the calculated time delay between the original pulse and the reflected signal, can be used to determine whether transducer 22 is in alignment with branch vessel 16.

Figure 6A:
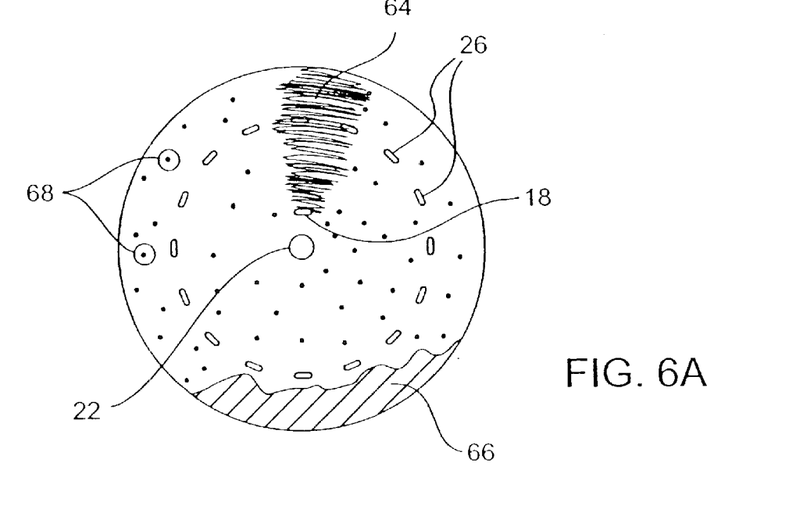
FIGS. 6A and 6B depict ultrasound images of a stent within a body lumen.
Figure 6B:
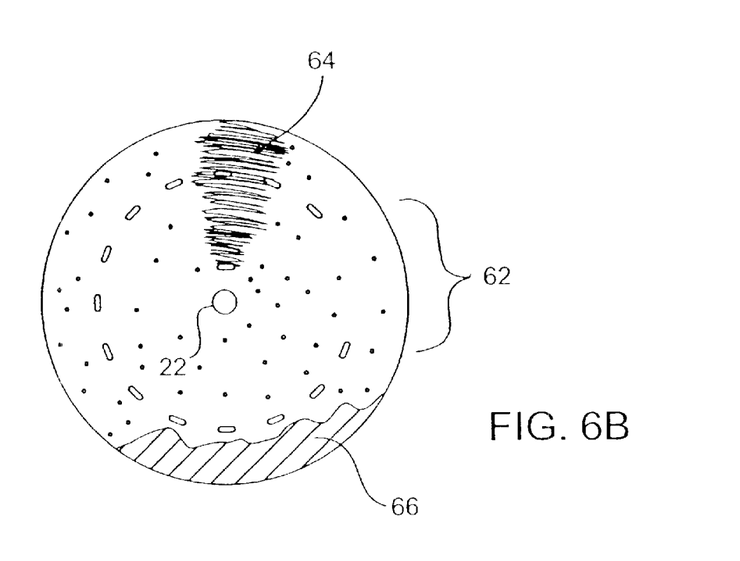

Turning now to FIG. 6A and 6B, cross-sectional ultrasound images of a stent disposed in a body lumen are shown. FIG. 6A depicts a two-dimensional image showing stent struts 26 disposed about a center catheter or transducer 22. The imaging performed by transducer 22 reveals blood speckles 68, guidewire 18 and a guidewire shadow 64, as well as a plaque 66 or other vessel wall imperfections. FIG. 6A depicts a generally uniform strut 26 structure and may exemplify the cross-sectional view of a stent that does not have a side hole, or the cross-sectional view of stent 10 when transducer 22 is not aligned with side hole 12. For example, transducer 22 may be located proximal or distal to side hole 12. FIG. 6B depicts a similar view as shown in 6A, except the imaging transducer 22 is aligned with side hole 12. As a result, a gap 62 is seen in the strut 26 pattern. It is the imaging of gap 62 which helps align side hole 12 with branch vessel 16 according to one embodiment of the present invention.

Images depicted in FIGS. 6A and 6B may be created in several ways according to the present invention. In one embodiment as previously described, transducer 22 is rotated about the longitudinal axis 200 by drive cable 44. In this manner, a single transducer 22 can produce a two dimensional, 360 degree image plane as shown in FIGS. 6A and 6B. In an alternative embodiment, a ring of transducer elements (not shown) are disposed in the catheter distal end to produce a two dimensional, 360 degree image plane without the need to rotate the ring of elements, although the elements may be rotated in another embodiment. The fixed ring of transducer elements may be disposed on an outer surface of balloon 25, between balloon 25 and stent 10. Preferably, such an embodiment has at least some of the transducer elements disposed on balloon 25 where sidehole 12 overlies. In this manner, some of the transducer elements will produce gap 62 as shown in FIG. 6B. In an alternative embodiment, the ring of transducer elements are disposed on the outer surface of a sheath, similar to outer member 32 shown in FIG. 3B. In this embodiment, the ring of transducer elements are disposed inside balloon lumen 30. In still another embodiment, the ring of transducer elements are not used to produce an image as in FIGS. 6A and 6B, but instead are used to indicate side hole to branch vessel alignment in accordance with the discussion accompanying FIG. 10.

Figure 7A:
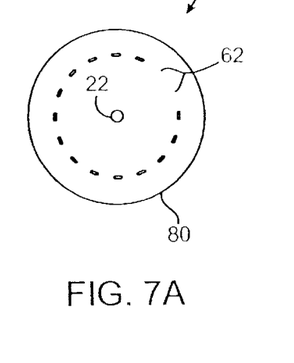
FIGS. 7A–7C depict simplified cross-sectional images of a vessel having a stent delivery system according to the present invention disposed therein.
Figures 7B, 7C:
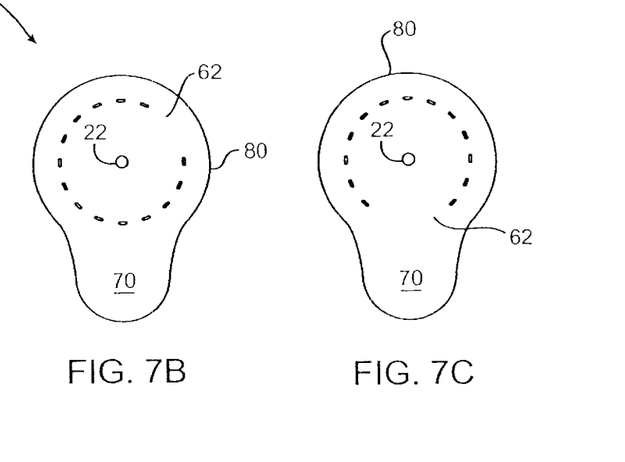
Figures 8A, 8B, 8C:
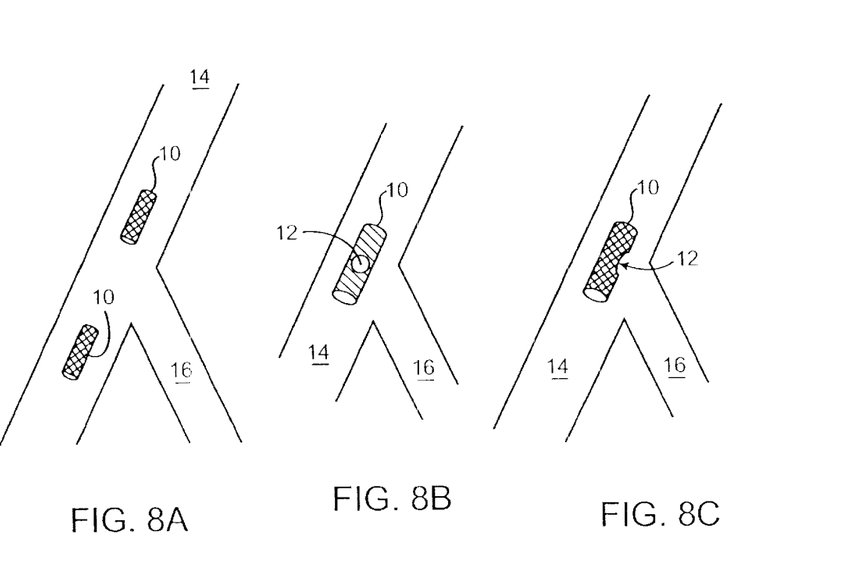
FIGS. 8A–8C depict simplified views of a stent delivery system disposed in a body lumen in positions which correspond to the images shown in FIGS. 7A–7C.

FIG. 7, in conjunction with FIG. 8, are helpful in explaining methods of the present invention. FIGS. 7A–7C depict simplified ultrasound cross-sectional images of a stent delivery apparatus disposed within a body lumen, such as main vessel 14. The images shown in FIGS. 7A–7C correspond to the stent and ultrasound transducer 22 positions shown in FIGS. 8A–8C. For example, FIGS. 7A and 8A depict stent 10 disposed within main vessel 14 where stent 10 is not adjacent to or aligned with branch vessel 16. Hence, the image of FIG. 7A shows a generally uniform main vessel wall 80 not adjacent to the bifurcation. As a result, gap 62 corresponding to side hole 12 is not aligned with branch vessel 16. In such a configuration, it is desirable to axially translate transducer 22 and stent 10 to continue to search for the desired branch vessel 16.

FIGS. 7B and 8B depict stent 10 in axial or longitudinal alignment with branch vessel 16, however, side hole 12 is facing away from the ostium of branch vessel 16. The image shown in FIG. 7B has an extended region 70 corresponding to the delayed signal return associated with the signals traveling at least partially down branch vessel 16. In other words, the branch vessel 16 opening is now in view of transducer 22. However, as shown in FIG. 7B, gap 62 is still depicted facing main vessel wall 80. In such a configuration, it is then desirable to rotate stent 10 to properly align side hole 12 with the ostium of branch vessel 16. The desired configuration showing the alignment of side hole 12 with the ostium of branch vessel 16 is shown in FIGS. 7C and 8C. FIG. 7C now depicts gap 62 in registry with extended region 70. Such an image corresponds with the alignment of side hole 12 with the ostium of branch vessel 16, as shown in FIG. 8C. In this manner, the use of ultrasound imaging helps facilitate the alignment of side hole 12 with branch vessel 16. Preferably, ultrasound transducer 22 is aligned with side hole 12 at all times, so ultrasound signals are transmitted to and from transducer 22 through side hole 12. In this manner, gap 62 will be seen on the ultrasound images. Alternatively, transducer 22 may move freely relative to stent 10. In such an embodiment, it may be desirable to first image with transducer 22 to locate side hole 12, with reference to the images of FIGS. 6A and 6B as guidance.

Figure 9:
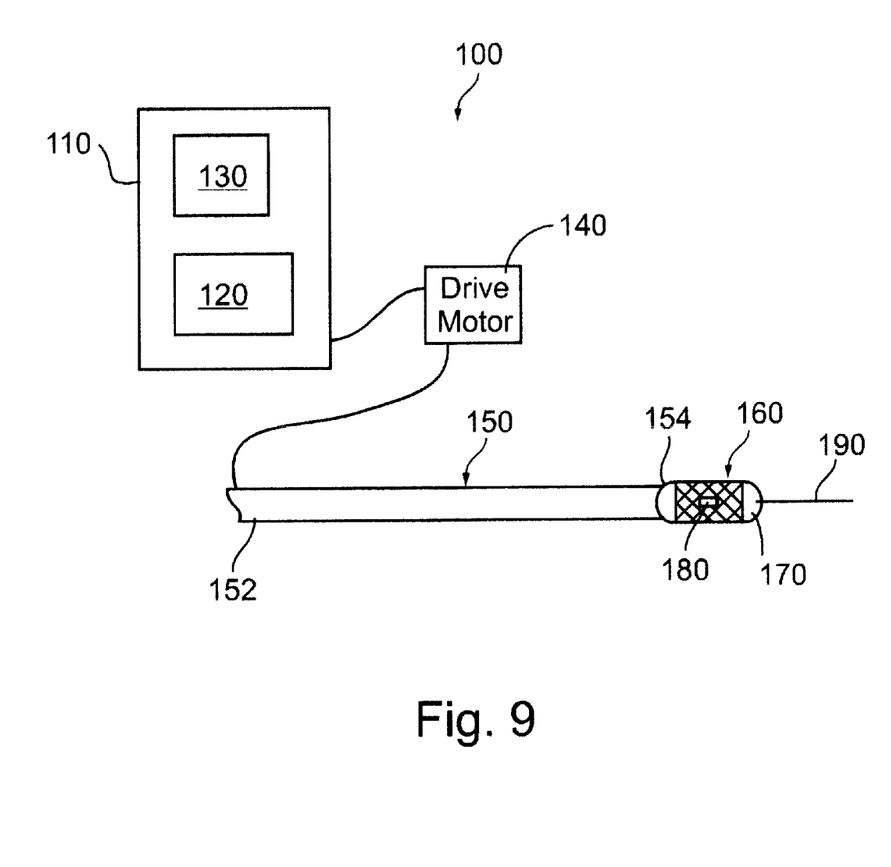
FIG. 9 depicts a simplified schematic of a stent delivery system according to the present invention.

FIG. 9 depicts an exemplary stent delivery system 100 according to the present invention. Delivery system 100 includes a console 110 having a controller 120 and a display 130. Controller 120 is coupled to a drive motor 140, which in one embodiment is used to rotate an ultrasound transducer 180. Transducer 180 is similar to transducer 22 described in conjunction with earlier Figures. Further, transducer 180 may be array of transducers as previously described. As shown in FIG. 9, a catheter 150 is provided having a proximal end 152 and a distal end 154 to which transducer 180 is coupled. Catheters for delivering stents according to the present invention are described in further detail in U.S. application Ser. No. 09/663,111, entitled "Catheter with Side Sheath And Methods"; and U.S. application Ser. No. 09/600,348, entitled "Extendible Stent Apparatus," the complete disclosures of which are incorporated herein by reference.

Figure 10:
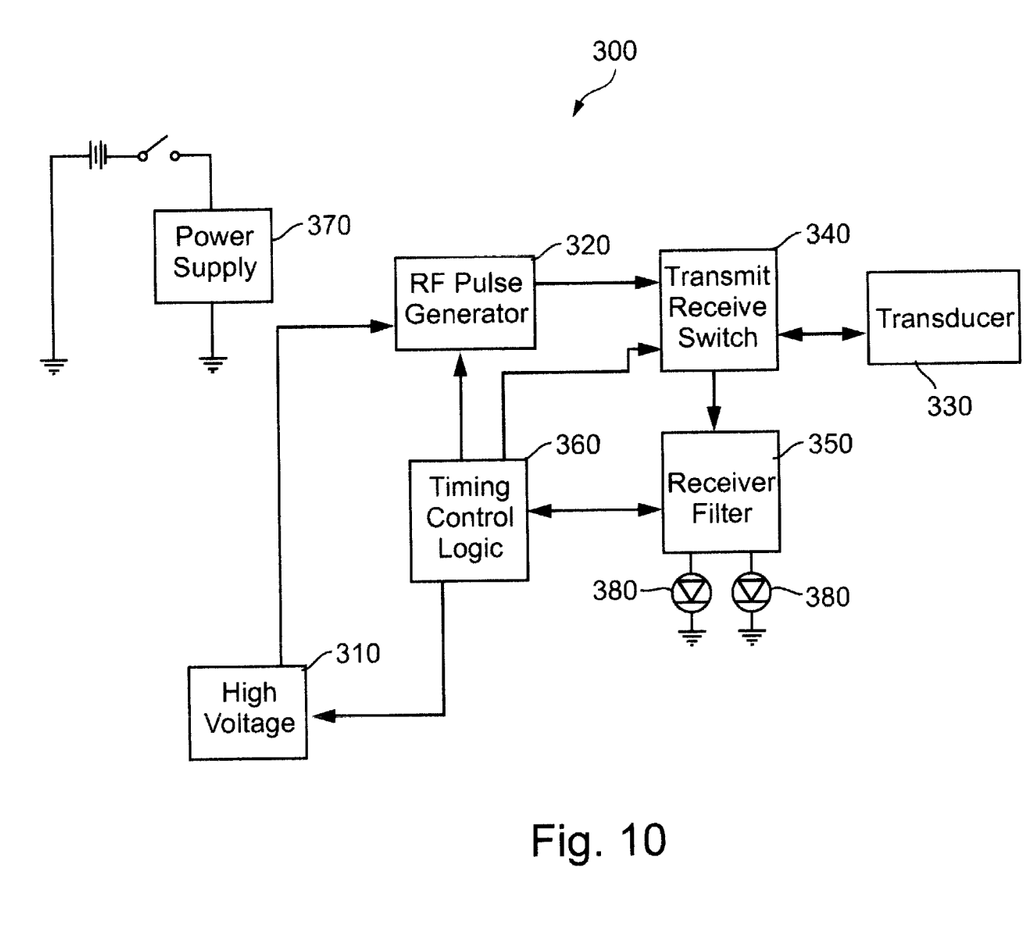
FIG. 10 depicts a simplified schematic of imaging catheter electronics for use with the present invention.

As shown, system 100 includes a guidewire 190 over which a balloon 170 and a stent 160 are disposed. A control circuitry, as shown in FIG. 10, is used to transmit an electrical signal from a voltage source to transducer 180 to generate imaging ultrasound signals as is well known in the art. Transducer 180 is then used to position stent 160 such that a side hole (not shown) of stent 160 is properly aligned with an ostium of a branch vessel.

FIG. 10 depicts a simplified schematic of one embodiment of control circuitry 300 for use with the present invention. A high voltage source 310 is coupled to an RF pulse generator 320 which generates an electrical pulse for transmission to transducer 330 by way of a transmit/receive switch 340. Transducer 330 receives the electrical signal as voltage applied across opposing surfaces of transducer 330. The transducer material, preferably piezoelectric material, generates a soundwave which propagates from the surface of transducer 330. As previously noted, the soundwaves reflect off changes in medium density, such as the wall of a vascular vessel, and a portion of the signal returns to transducer 330. Transducer 330 then transmits the received signal to transmit/receive switch 340 and a receiver filer 350. Timing control and logic circuitry 360 coordinates RF pulse generator 320, transmit/receive switch 340 and receiver filter 350 operation.

As previously described, the time delay of signals received from echoes off the branch vessel are greater than the time delay from signals received off of the main vessel walls. In one embodiment, receiver filter 350 may be used to indicate to a user of system 100 that side hole 12 is aligned, or not aligned, with branch vessel 14. For example, one or more indicator lights 380 may be used to indicate side hole alignment (green) or non-alignment (red). In some embodiments, circuitry 300 does not produce a visual image of the body lumen. Instead, the signals received from transducer 330 are used to indicate sidehole to branch vessel alignment. A power supply 370 facilitates operation of the individual electrical components.

Figure 11:
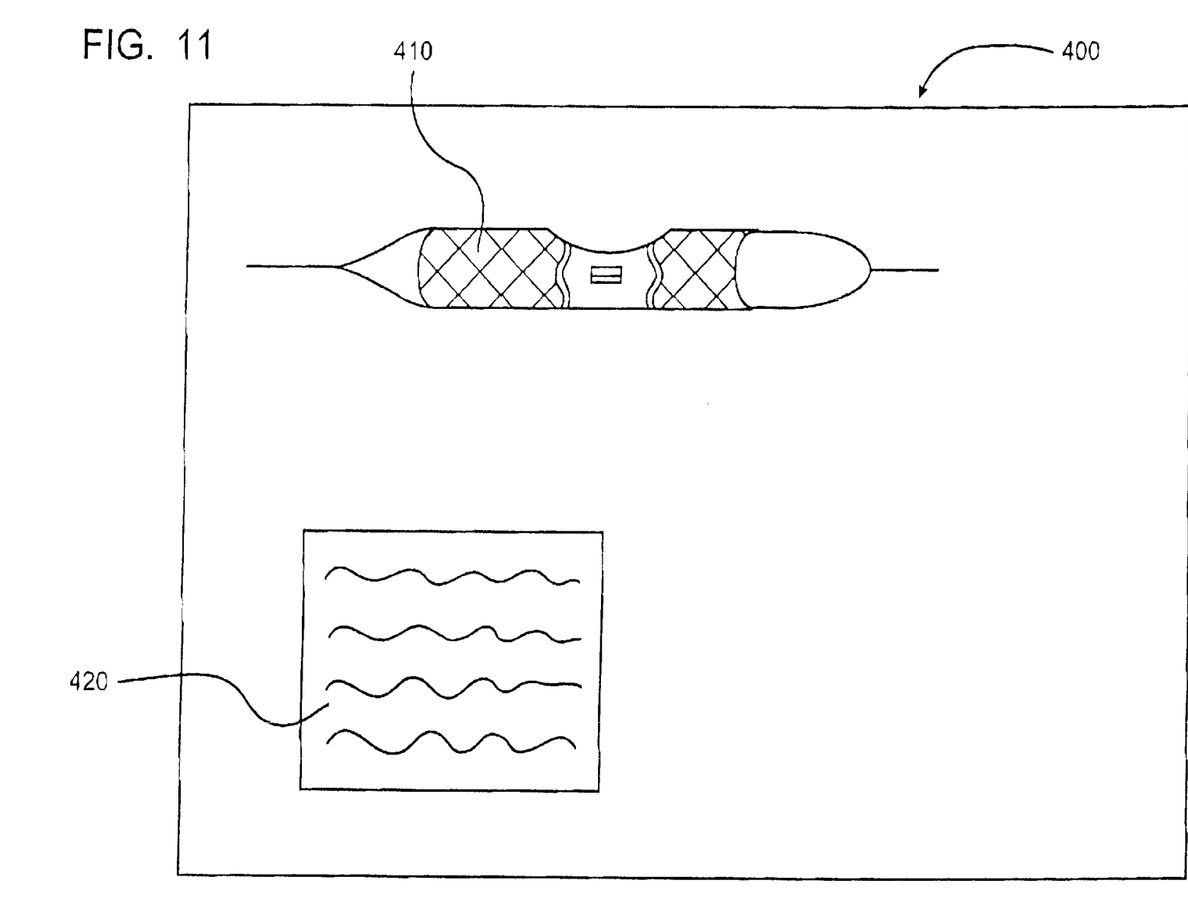
FIG. 11 depicts a kit including apparatus and instructions for use according to the present invention.

As shown in FIG. 11, stent, catheter and/or system 410 may be conveniently included as part of a kit 400. Kit 400 includes instructions for use 420 which set forth various procedures for deploying stent 10 and imaging using transducer 22 using any of the techniques previously described. Instructions for use 420 may be in written or in machine readable form. Further, it will be appreciated that kit 400 may alternatively include any of the other elements described herein, such as imaging catheter 15, balloon 20, and the like. Further, instructions 420 may describe use of any of the other elements.

The invention has now been described in detail for purposes of clarity of understanding. However, it will be appreciated that certain changes and modifications may be practiced within the scope of the appended claims. For example, while transducer 22 is generally described as coupled to a drive cable 44 facilitating transducer rotation, transducer 22 also may be fixed relative to stent 10. In such an embodiment, transducer 22 would comprise a sidelooking transducer facing side hole 12. In this manner, transducer 22 would be aligned with side hole 12 to facilitate side hole 12 alignment with branch vessel 16. Such a configuration would produce images similar to that shown in FIGS. 6B, but comprising a pie-shaped portion of the image. Rotation of transducer 22 could then occur by rotating stent 10, with transducer 22 maintaining a vigilant eye towards side hole 12.

What is claimed is:

1. A stent delivery system, comprising: a catheter comprising a catheter body having a distal end, a proximal end, a longitudinal axis and a lumen;

an expansion device disposed near the catheter body distal end;

a stent having a side hole, said stent being disposed over the expansion device; and an ultrasound transducer disposed near the catheter body distal end between said expansion device and said stent and positioned for transmitting and receiving ultrasound signals through said side hole.

2. The stent delivery system as in claim 1 wherein said expansion device comprises a balloon.

3. The stent delivery system as in claim 1 wherein said ultrasound transducer is adapted to be axially translated along said longitudinal axis.

4. The stent delivery system as in claim 1 wherein said ultrasound transducer is adapted to be rotated relative to said longitudinal axis.

5. The stent delivery system as in claim 1 further comprising a transducer housing to which said transducer is coupled, said housing having a distal end, a proximal end that is coupled to the system, and a passageway passing through said housing between said proximal and distal ends.

6. The stent delivery system as in claim 5 wherein said housing proximal end is coupled to a drive cable adapted to rotate said housing relative to said catheter distal end.

7. The stent delivery system as in claim 5 further comprising a guidewire at least partially disposed in said lumen.

8. The stent delivery system as in claim 1 further comprising a guidewire as least partially disposed in said lumen.

9. The stent delivery system as in claim 1 further comprising a controller coupled to said transducer.

10. A method of positioning a stent having a side opening, said method comprising:

providing a stent delivery system, comprising;

a catheter comprising a catheter body having a distal end, a proximal end, a longitudinal axis and a lumen;

an expansion device disposed near the catheter body distal end;

a stent having a side hole, said stent being disposed over the expansion device; and an ultrasound transducer disposed near the catheter body distal end for transmitting and receiving ultrasound signals through said side hole;

positioning said stent delivery system in a body lumen;

imagining said body lumen with said transducer to locate an ostium of a branch vessel; and aligning said stent side hole with said ostium.

11. The method of claim 10 wherein said transducer is disposed in said expansion device.

12. The method of claim 10 wherein said ultrasound transducer is adapted to rotate relative to said longitudinal axis, and said imaging further comprises rotating said transducer to image a cross section of said body lumen.

13. The method of claim 10 wherein said aligning comprises axially translating said stent.

14. The method of claim 10 wherein said aligning comprises rotating said stent about said longitudinal axis.

15. The method of claim 10 further comprising:

introducing a body lumen guidewire into said body lumen; and advancing said catheter over the guidewire and through said body lumen to be near said branch vessel.

16. The method of claim 15 wherein said transducer is coupled to a housing having a passageway through which said guidewire passes, said advancing also advancing said transducer housing to be near said branch vessel.

17. The method of claim 13 wherein said stent delivery system further comprises a controller coupled to said transducer for controlling said imaging.

* * * * *